United States Patent
Heuser

(10) Patent No.: US 6,464,681 B1
(45) Date of Patent: *Oct. 15, 2002

(54) METHODS AND APPARATUS FOR TREATING BODY TISSUES AND BODILY FLUID VESSELS

(76) Inventor: Richard R. Heuser, 2626 E. Arizona Biltmore Cir., No. 9, Phoenix, AZ (US) 85016

( * ) Notice: Subject to any disclaimer, the term of this patent is extended or adjusted under 35 U.S.C. 154(b) by 54 days.

This patent is subject to a terminal disclaimer.

(21) Appl. No.: 09/705,963

(22) Filed: Nov. 3, 2000

Related U.S. Application Data

(63) Continuation of application No. 09/397,806, filed on Sep. 17, 1999, now Pat. No. 6,159,197.

(51) Int. Cl.[7] .............................................. A61M 31/00
(52) U.S. Cl. ..................................... 604/508; 604/506
(58) Field of Search ................................ 604/508, 509, 604/907, 913, 506, 500, 82, 83, 96.01, 104; 606/191, 192, 215, 108, 213

(56) References Cited

U.S. PATENT DOCUMENTS

| | | | | |
|---|---|---|---|---|
| 4,744,364 A | * | 5/1988 | Kensey | 606/213 |
| 4,832,688 A | * | 5/1989 | Sagae et al. | 604/53 |
| 5,437,292 A | * | 8/1995 | Kipshidze et al. | 128/898 |
| 5,512,291 A | * | 4/1996 | Li | 424/443 |
| 5,665,107 A | * | 9/1997 | Hammerslag | 606/214 |
| 5,843,124 A | * | 12/1998 | Hammerslag | 606/214 |

\* cited by examiner

Primary Examiner—Brian L. Casler
Assistant Examiner—Kevin C. Sirmons
(74) Attorney, Agent, or Firm—Kolisch Hartwell

(57) ABSTRACT

Methods for treating bodily tissues and fluid vessels are disclosed. According to a method of repairing a perforation in a bodily fluid vessel, a viscous, moldable substance is inserted into the vessel at the location of the perforation. A path is opened through the moldable substance to permit fluid flow through the vessel. According to a method of introducing a tissue-killing substance into a bodily fluid vessel, a catheter is provided that has a blocking mechanism configured to selectively block and unblock the vessel. The catheter also has a delivery system that is configured to introduce the tissue-killing substance into the vessel. The vessel is substantially blocked upstream of a selected tissue using the blocking mechanism. The tissue-killing substance is introduced into the vessel through the delivery system, and the vessel is unblocked when the tissue-killing substance has substantially traveled toward the selected tissue. According to a method of occluding a bodily fluid vessel, a catheter is provided that has a first passage. The first passage has an occlusion element housed therein. The catheter is positioned in the vessel, and the occlusion element is moved out of the passage and into the vessel to thereby occlude the vessel. A catheter is also disclosed that may be used with the above methods.

7 Claims, 7 Drawing Sheets

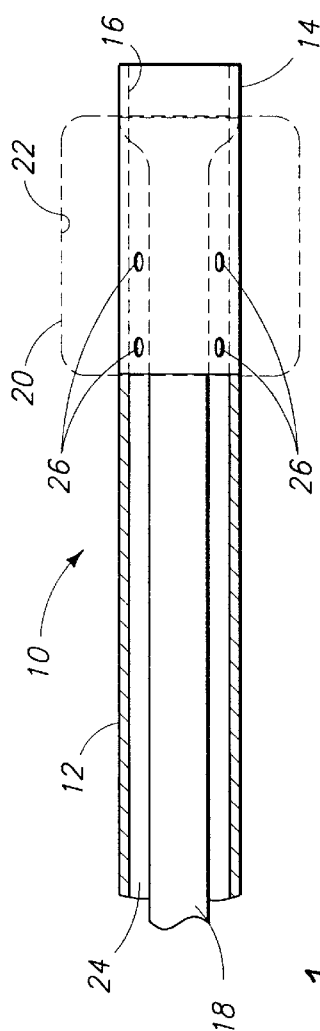
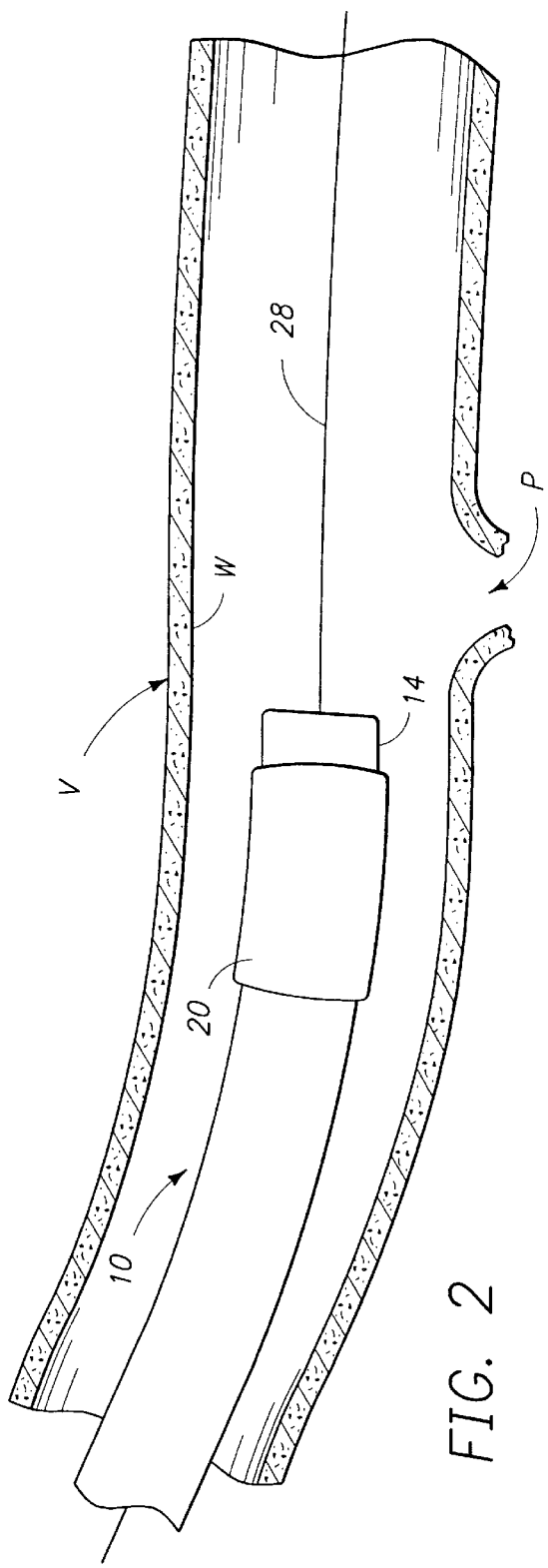
FIG. 1
FIG. 2

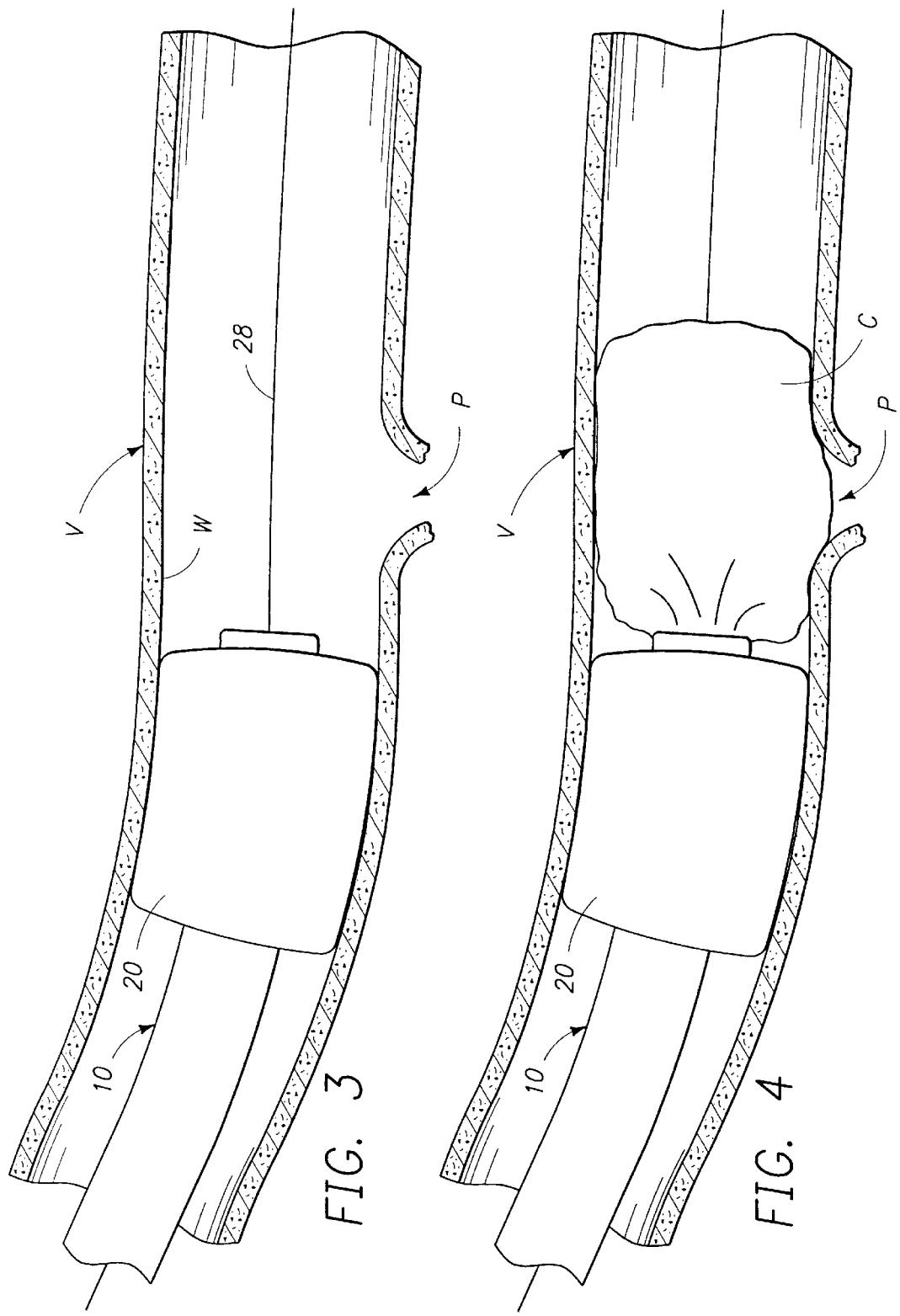

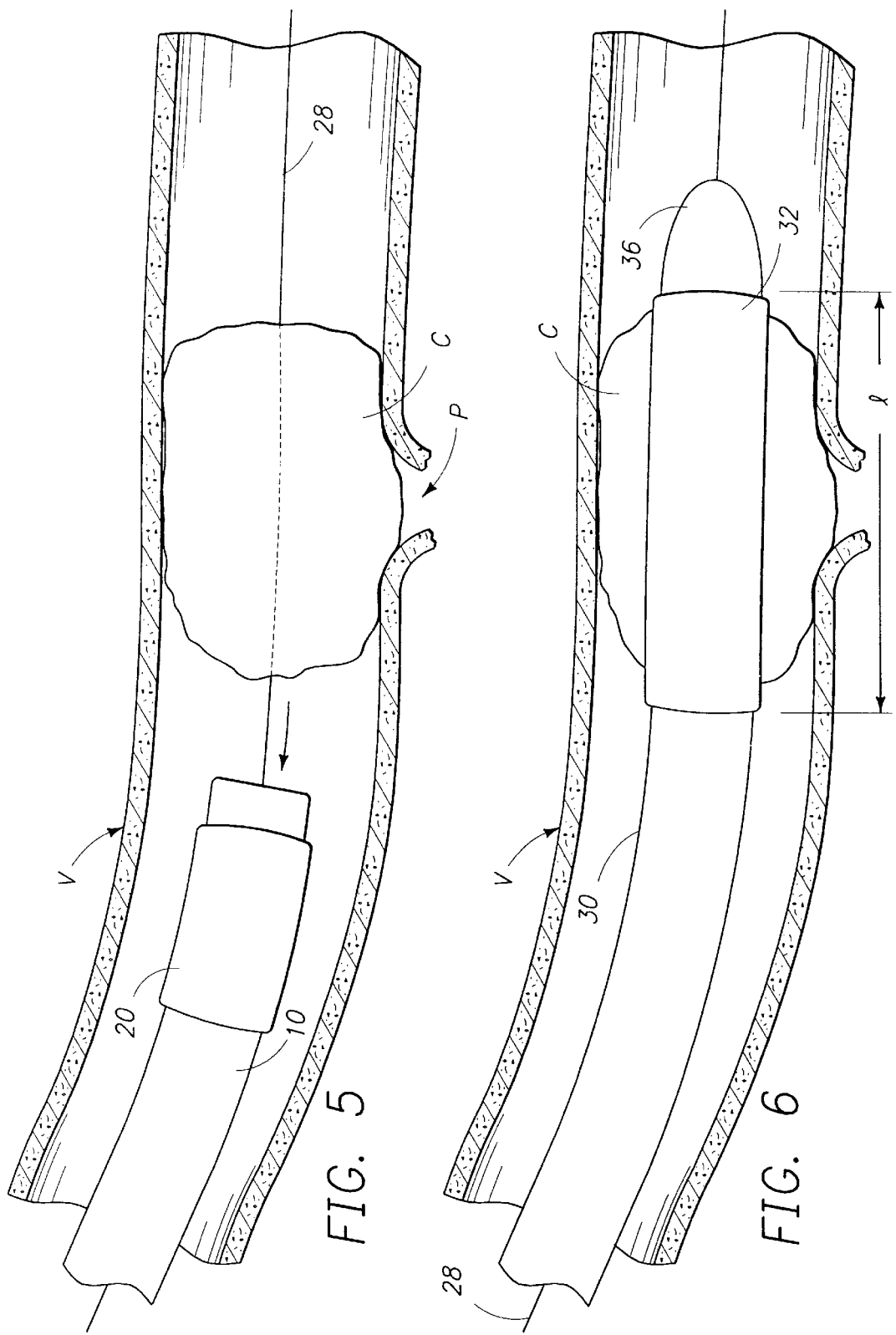

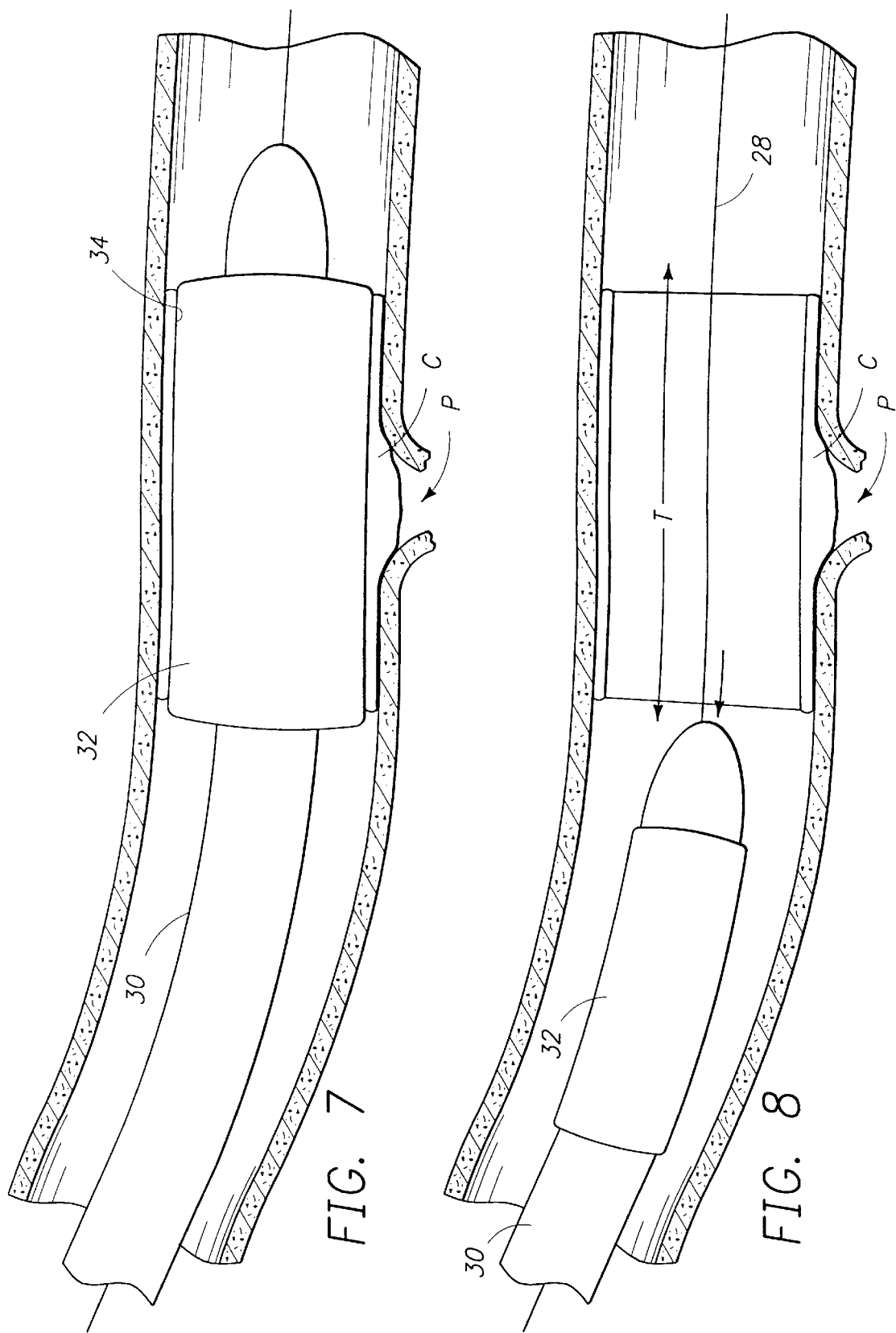

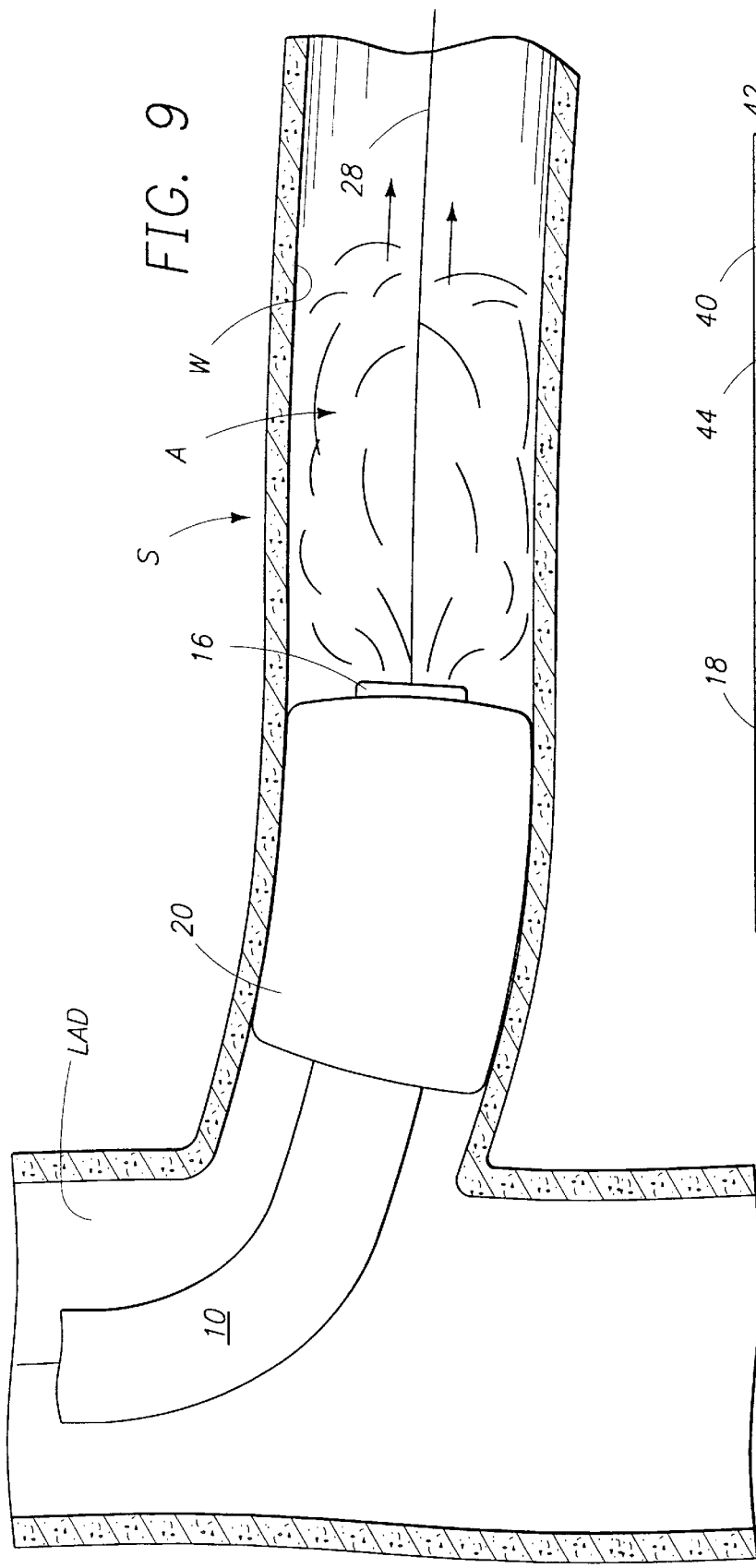
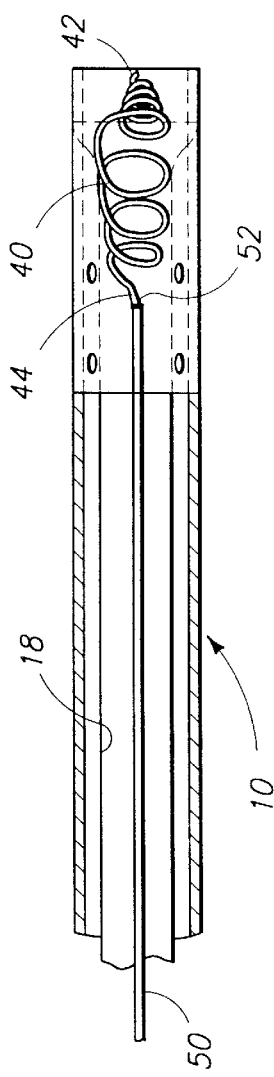
FIG. 9
FIG. 10

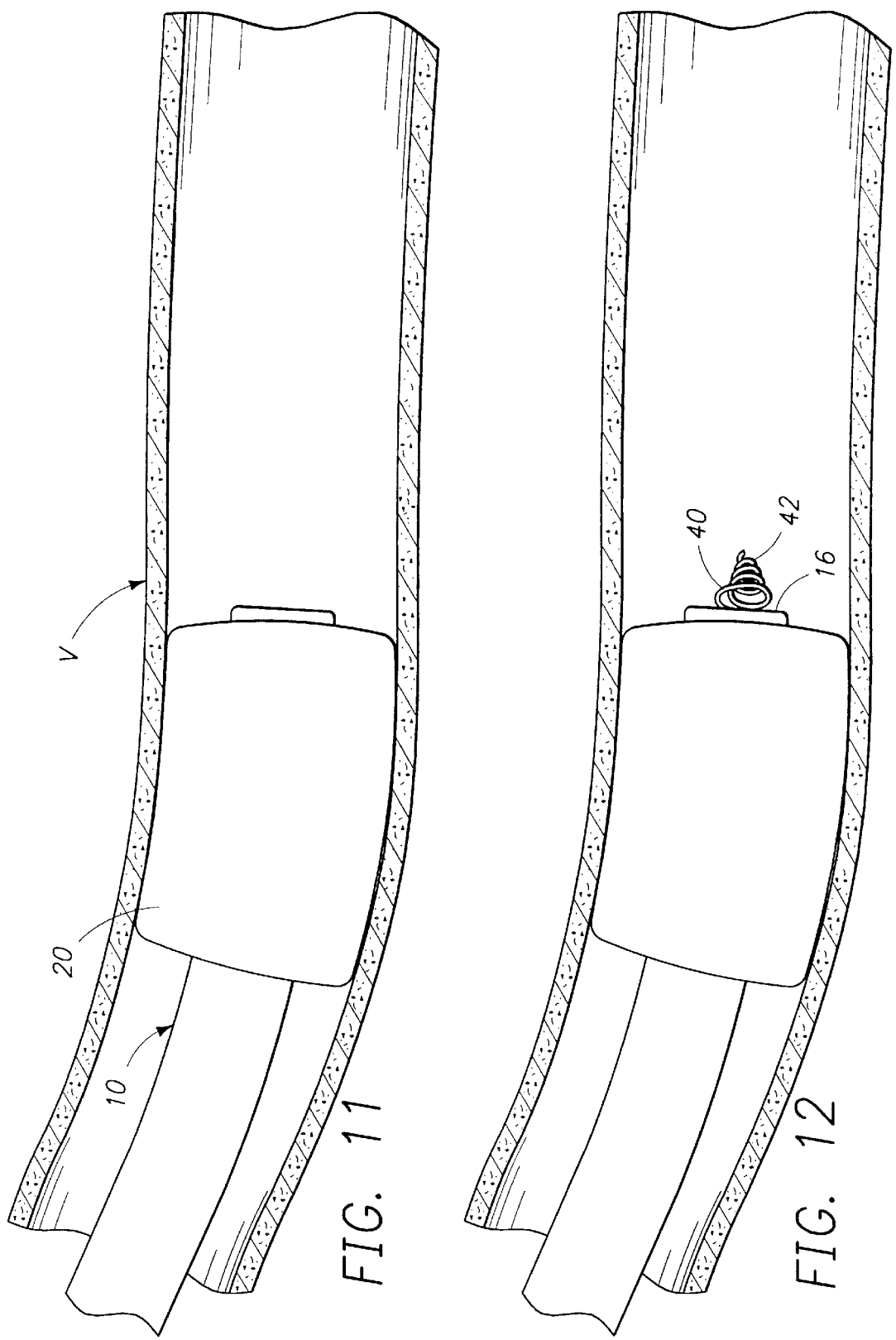

METHODS AND APPARATUS FOR TREATING BODY TISSUES AND BODILY FLUID VESSELS

CROSS-REFERENCE TO RELATED APPLICATION

This application is a continuation of U.S. patent application Ser. No. 09/397,806, filed Sep. 17, 1999, which is hereby incorporated by reference, and which is issued on Dec. 12, 2000 as U.S. Pat. No. 6,159,197.

FIELD OF THE INVENTION

The invention is directed to methods of using a balloon catheter to treat perforated bodily fluid vessels, diseased tissues, and other irregularities in bodily fluid vessels such as arteriovenous fistulae and aneurysms.

BACKGROUND OF THE INVENTION

Treatment of heart disease has traditionally been a highly traumatic endeavor. For many years surgeons would be required to conduct major surgery to correct even relatively minor conditions. Such "open-heart" operations are highly traumatic for the patient and may therefore not be an option for those whose bodies cannot withstand such trauma. Open-heart operations are also expensive and may be risky. There is also a possibility of the patient contracting an infection during his or her extended stay in a medical care facility. For these reasons, some conditions may not merit treatment if open-heart surgery is required for their treatment.

The use of low-trauma surgery devices and techniques has increased the treatment and success rates for many conditions that are either too risky or too expensive to perform during open-heart surgery. The catheter is one such low-trauma device that has been especially successful in the treatment of cardiovascular and other conditions. A typical catheter is a flexible, hollow small-diameter tube that is threaded through a body system (such as the cardiovascular system) until it reaches a location that requires treatment. An advantage of a catheter is that only a small incision need be made to insert the catheter into the body. This significantly reduces the trauma experienced by the patient and dramatically reduces recovery time. Furthermore, depending on the procedure, only local anesthesia may be needed. This reduces the risk and cost of the procedure. Catheters have been successfully used in angioplasty procedures and in the delivery of stents and other medical devices into selected areas of the body.

One procedure that has met with limited success using low-trauma surgical techniques is the killing off or elimination of tissues such as the septum of the heart. If a tissue-killing substance such as alcohol is inserted into an artery leading to the septum, there is a risk that some of the alcohol may travel instead through arteries leading to other portions of the heart. This would damage other portions of the heart, and a heart attack may result. Known infusion techniques have not been able to reliably deliver alcohol to a desired tissue while preventing the alcohol from damaging other tissue.

Another procedure that has met with limited success is the repair of perforations or ruptures in blood vessels. Such perforations may prove fatal if the rate of the resulting internal bleeding is substantial. Surgery is often required to repair the perforation, but in high-risk circumstances surgery may not be advisable.

Still another procedure that has, until the present invention, created challenges for the surgeon is the occlusion of small, inconsequential vessels. When a smaller vessel is perforated, the physician may decide to permanently block, or occlude, the vessel. Known catheter techniques are unreliable because they do not have a means to hold the catheter in place while treating the damaged vessel. Furthermore, known techniques may not work with vessels having smaller diameters.

SUMMARY OF THE INVENTION

The invention provides a method of repairing a perforation in a bodily fluid vessel. According to the method, a viscous, moldable substance is inserted into the vessel at the location of the perforation. A path is opened through the moldable substance to permit fluid flow through the vessel.

Another aspect of the invention provides a method of introducing a tissue-killing substance into a bodily fluid vessel. According to the method, a catheter is provided that has a blocking mechanism configured to selectively block and unblock the vessel. The catheter also has a delivery system that is configured to introduce the tissue-killing substance into the vessel. The vessel is substantially blocked upstream of a selected tissue using the blocking mechanism. The tissue-killing substance is introduced into the vessel through the delivery system, and the vessel is unblocked when the tissue-killing substance has substantially traveled toward the selected tissue.

Still another aspect of the invention provides a catheter for use in occluding a bodily fluid vessel. The catheter includes a length of flexible tubing that has an opening at a distal end of the tubing. A first passage, provided within the tubing, is in communication with the opening. An occlusion element is housed inside the passage and is configured to exit the passage through the opening to at least partially occlude the vessel.

Yet another aspect of the invention is a method of occluding a bodily fluid vessel. According to the method, a catheter is provided that has a first passage. The first passage has an occlusion element housed therein. The catheter is positioned in the vessel, and the occlusion element is moved out of the passage and into the vessel to thereby occlude the vessel.

BRIEF DESCRIPTION OF THE DRAWINGS

FIG. 1 is a side elevational, partial cutaway view of a first catheter according to an embodiment of the invention.

FIG. 2 is a side elevational view of a body fluid vessel during a perforation repair process according to the invention.

FIG. 3 is a side elevational view of another portion of the perforation repair process.

FIG. 4 is a side elevational view of another portion of the perforation repair process.

FIG. 5 is a side elevational view of another portion of the perforation repair process.

FIG. 6 is a side elevational view of another portion of the perforation repair process, showing how a second catheter is used therewith.

FIG. 7 is a side elevational view of another portion of the perforation repair process.

FIG. 8 is a side elevational view of another portion of the perforation repair process.

FIG. 9 is a side elevational view of a portion of an alcohol infusion process.

FIG. 10 is a partial cutaway view of the first catheter shown in FIG. 1 prepared for use in a vessel occlusion process.

FIG. 11 is a side elevational view of a portion of a vessel occlusion process.

FIG. 12 is a side elevational view of another portion of the vessel occlusion process.

DETAILED DESCRIPTION OF THE DRAWINGS AND BEST MODE FOR

Carrying Out the Invention

Figure 13:
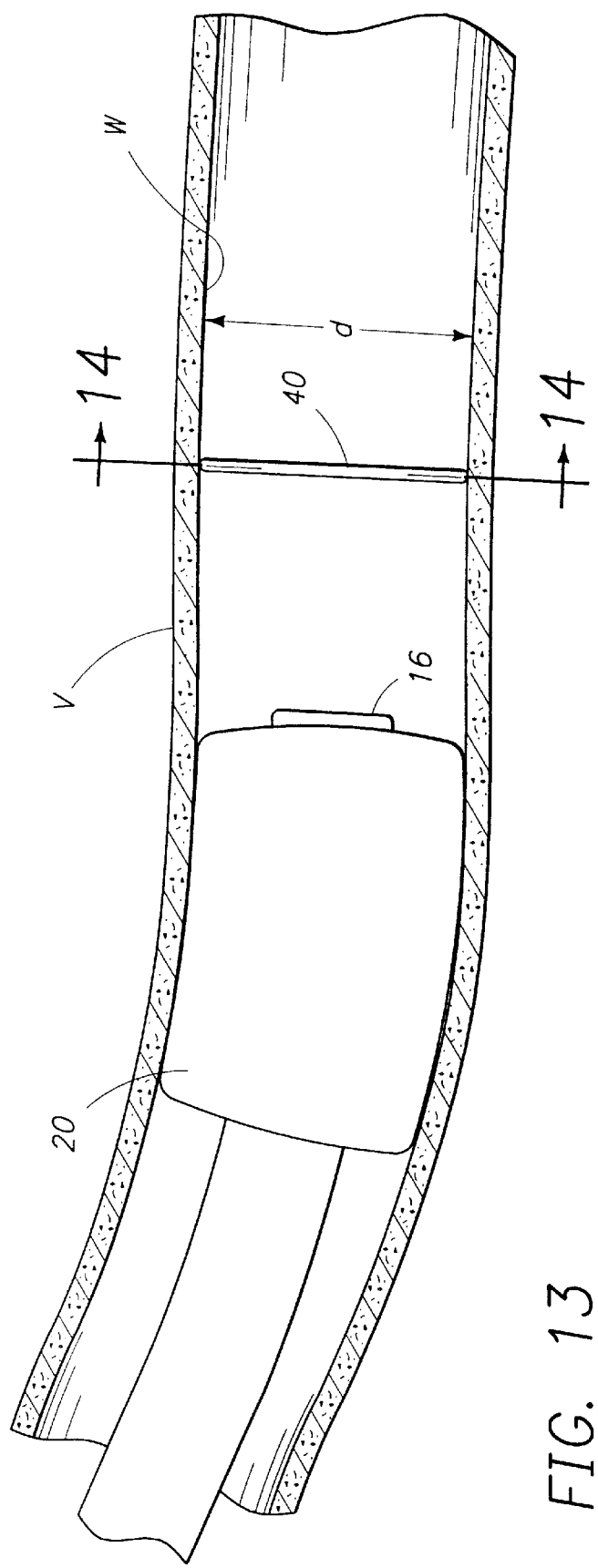
FIG. 13 is a side elevational view of another portion of the vessel occlusion process.

FIG. 1 depicts a first catheter 10 that may be used with the processes and procedures disclosed herein. First catheter 10 includes a flexible, generally cylindrical length of hollow tubing 12. The tubing preferably has an outside diameter of about 1–4 mm. A distal end 14 of the first catheter has an opening or aperture 16. A first passage, shown as a first lumen 18, runs the length of catheter 10 and communicates with aperture 16. First lumen 18 preferably has an inner diameter of about 0.018–0.038 inches. The first lumen permits fluids or colloids to be selectively introduced into a vessel, as will be described below. A first flexible membrane, shown as a first balloon 20, is secured to tubing 12 adjacent distal end 14. First balloon 20 has an interior 22 that varies in volume when expanded and contracted. A second passage, shown as a second lumen 24, runs the length of first catheter 10 and communicates with interior 22 of the first balloon through intermediate apertures 26 that pass through tubing 12. A controlling fluid (not shown) flows within second lumen 24 and is controlled by an operator to expand/inflate and contract/deflate the first balloon. The first balloon functions as a flow-blocking mechanism to block the flow of blood or other fluid through a vessel while a surgical technique or process is being completed. As such, first balloon 20 is very compliant and inflates with a very slight change in pressure within second lumen 24. First balloon 20 preferably has an outer diameter of about 2–8 mm when fully inflated.

FIGS. 2 through 8 show how first catheter 10 may be used to repair a perforation P in the wall W of a bodily fluid vessel V, which may be an artery or a vein. A guide wire 30 is first inserted into vessel V using known methods. First catheter 10, with first balloon 20 deflated, is threaded along guide wire 28 until distal end 14 of the catheter approaches perforation P (FIG. 2). The operator inflates first balloon 20 (FIG. 3) by controlling the flow of controlling fluid (not shown) within second lumen 24 and interior 22 of the first balloon. In its inflated state, first balloon 20 blocks the normal flow of blood B through vessel. A viscous, moldable substance such as colloid C, which has been inserted into first lumen 18, is then released into the area of the vessel surrounding perforation P (FIG. 4). The viscous, moldable substance may include any biocompatible substance that is fluid enough to be directed through a catheter and that is in a moldable state immediately after being inserted into the vessel. The viscous, moldable substance must also have a viscosity or consistency such that it does not freely flow through perforation P or along vessel V. The viscous, moldable substance may be designed to coagulate, cure, set or harden over time. Examples of suitable substances include thrombin, gel, gel foam, the thrombin collagen developed by Vascular Solutions, or other biocompatible substances. Blood removed from the patient and allowed to thicken, perhaps with the aid of protamine, may also be a suitable moldable substance.

After colloid C has been released into vessel V, first balloon 20 is deflated by reducing the pressure and/or flow of controlling fluid (not shown) within second lumen 24 (FIG. 5). The operator withdraws first catheter 10 from vessel V.

A second catheter 30 is then threaded along guide wire 28 into vessel V (FIG. 6). Second catheter 30 includes a second flexible membrane, shown as a second balloon 32, that is controllable in a manner similar to first balloon 20. Specifically, second catheter 30 has an inner passage or lumen (not shown) that communicates with the interior 34 of second balloon 32. The second balloon has a length l that is longer than the deposit of colloid C in the vessel. The operator moves the distal end 36 of the second catheter through colloid C so that second balloon 32 extends from either end of the colloid deposit, as shown in FIG. 6. Second balloon 32 is then inflated (FIG. 7), and colloid C is pressed against wall W of the vessel. Since colloid C is thick or viscuous, the colloid will not be pressed through perforation P. Instead, the expanding second balloon creates a path T through the colloid such that blood B may flow unimpeded therethrough upon deflation and withdrawal of second balloon 32, second catheter 30 and guide wire 28 (FIG. 8). Because the colloid isolates perforation P from path T, the perforation is effectively repaired. It will be understood that any malleable substance that can be placed in vessel V by conventional means to cover perforation P and then pressed against wall W of vessel V by second balloon 32 may be used to repair perforation P, so long as the malleable substance can undergo plastic deformation by balloon 32 without rupture of the malleable substance.

The above process is useful for repairing perforations in blood vessels, but may also be used in repairing perforations or ruptures in other fluid-carrying vessels in the body. The above process may, for example, also be used to repair arteriovenous fistulae or aneurysms.

First catheter may also be used to kill or eliminate a desired tissue. For instance, in a case of idiopathic hypertrophic subaortic stenosis or if the septum of the heart is diseased, it may be necessary or desirable to kill the tissues comprising the septum of the heart. This may be accomplished by inserting a tissue-killing substance, such as alcohol, into the septum. First catheter 10 provides a way for such an alcohol infusion process to be performed without endangering the life of the patient.

To perform this procedure, guide wire 28 is placed into the left anterior descending (LAD) coronary artery of the heart and into a septal branch S of the LAD artery (FIG. 9). First catheter 10 is guided along guide wire 28 until first balloon 20, in a contracted state, has entered septal branch S. The operator inflates first balloon 20 as previously described. An amount of alcohol A is released or delivered through first lumen 18 into septal branch S and is permitted to flow toward the septum (not shown), where the alcohol kills the tissue of the septum. First balloon 20 serves as a blocking mechanism to prevent the flow of alcohol A out of the septal branch and into the LAD artery, where the alcohol would otherwise flow and destroy other tissues in the heart. By pressing against the interior wall W of septal branch S, first balloon 20 holds first catheter 10 in place while the alcohol is infused into the septal branch. The operator completes the alcohol infusion process by deflating first balloon 20 and removing first catheter 10 and guide wire 28 from septal branch S and LAD artery.

It may sometimes be necessary to provide an electrical impulse to the heart after the alcohol infusion process is complete. This "pacing" of the heart may be accomplished by transmitting the electrical impulse through guide wire 28 prior to removing the guide wire from the septal branch or the LAD artery.

First catheter 10 may also be used to permanently occlude a bodily fluid vessel. For instance, it may be determined that a perforated or otherwise damaged blood vessel will be difficult or risky to repair and that occlusion of the vessel is the most feasible way to stop the internal bleeding through the perforation. Alternately, it may be desirable to occlude a vessel that is the source of the filling of an aneurysm, or if the vessel in fact forms into an aneurysm or an arteriovenous fistula. Such vessels may include arteries related to the heart, brain, intestines or the lower limbs. FIG. 10 shows first catheter 10 that has been modified to be used in such a vessel occlusion process. First and second wire segments 40, 50 are inserted into first lumen 18. First wire segment 40, which may be considered an occlusion element or a coil, is substantially shorter than second wire segment 50. A first end 42 of coil 40 is disposed at distal end 14 of first catheter 10. Coil 40 is made of a flexible, resilient biocompatible material. The coil is formed to have a substantially planar spiral shape (FIGS. 13 and 14) with a maximum diameter d similar to the inner diameter of the vessel that is to be occluded. However, coil 40 is capable of being resiliently deformed so that it may be placed into first lumen 18. Coil 40 is depicted as having a spiral, substantially planar shape when delivered into the vessel, but coil may alternatively be shaped in other forms as required. For example, the coil may have a non-planar spiral shape, such as conical, frusto-conical or helical. The coil may also have a serpentine or an irregular shape.

A first end 52 of second wire segment 50 is positioned to be in contact with a second end 44 of coil 40 while the coil is inside first lumen 18. Second wire segment 50 passes substantially through the entire length of first lumen 18, and a second end (not shown) of the second wire segment is configured to be articulated or manipulated by an operator to axially move the second wire segment along the passage. Second wire segment 50 is constructed of a flexible, bendable biocompatible material and is capable of transmitting an axial force along its length.

Figure 14:
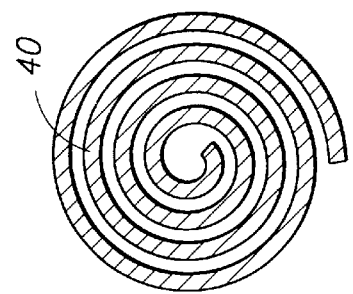
FIG. 14 is sectional view taken along line 14—14 in FIG. 13.

FIGS. 11–13 show a method of using first catheter 10 to occlude a blood vessel V. The operator inserts first catheter 10 into vessel V. First balloon 20 is expanded or inflated (FIG. 11) to block blood flow into vessel V and to hold first catheter 10 in place during the occlusion process. The operator manipulates the second end (not shown) of second wire segment 50 to axially move the second wire segment toward distal end 14 of the first catheter. First end 52 of second wire segment 50 contacts second end 44 of coil 40 and urges the coil out of aperture 16 (FIG. 12) and into vessel V. Once free of the first catheter, the coil resiliently reverts to its original planar spiral shape and contacts the wall of the vessel (FIG. 13). The coil substantially blocks normal blood flow in the vessel and aids in the normal blood clotting process. The operator completes the occlusion process by contracting or deflating first balloon 20 and removing first catheter 10 from the vessel.

It may be necessary or advisable to insert multiple coils into a vessel during an occlusion process. In such a case, multiple coils may be delivered into the vessel by repeating the above process as many times as desired. Alternatively, multiple coils may be serially inserted into the first lumen of the first catheter and inserted into the vessel as desired by manipulating the second wire segment.

The above vessel occlusion method may be used to occlude a damaged vessel, and may also be used if there is an ischemic condition, i.e., a lack of blood flow in a vessel due to a steal phenomenon, which is a diversion of blood from its normal course. The method may also be used in the neurovascular anatomy when either a tear or perforation is present in a vessel or an aneurism is present. Alternatively, the perforation repair method previously described may also be used to remedy these conditions.

An advantage of using first catheter 10 in the above methods is that the very compliant nature of first balloon 20 prevents injury or trauma to the vessel that is blocked. Another advantage is that first balloon 20 holds the catheter in place and prevents the catheter from being inadvertently moved during a process. Another advantage is that first passage 18 is large enough to deliver semi-liquid substances, such as a colloid, to a desired region in a vessel. First passage is also large enough to deliver solid occlusive elements such as coilable wire to a desired vessel. Another advantage is that first catheter 10 may be used with or without a guide wire as described above. In the case of the vessel occlusion process, second wire element 50 provides the needed stiffness instead of a guide wire. Yet another advantage is that aperture 16 is located immediately adjacent first balloon 20. This enables an accurate delivery of alcohol or colloid relative to the first balloon. Still another advantage is that first catheter 10 may be used for many different surgical procedures. A manufacturer saves costs because it does not need to make a separate catheter product for each of the different procedures. Surgeons also save training time because they do not need to learn how to a different catheter for every desired procedure. Finally, first catheter provides a way to safely and accurately accomplish procedures that previously have been accomplished only with great difficulty and risk to the patient.

While the invention has been disclosed in its preferred form, the specific embodiments thereof as disclosed and illustrated herein are not to be considered in a limiting sense as numerous variations are possible. Applicant regards the subject matter of the invention to include all novel and non-obvious combinations and subcombinations of the various elements, features, functions and/or properties disclosed herein. No single feature, function, element or property of the disclosed embodiments is essential. The following claims define certain combinations and subcombinations which are regarded as novel and non-obvious. Other combinations and subcombinations of features, functions, elements and/or properties may be claimed through amendment of the present claims or presentation of new claims in this or a related application. Such claims are also regarded as included within the subject matter of applicant's invention irrespective of whether they are broader, narrower, or equal in scope to the original claims.

I claim:

1. A method of repairing a perforation in a bodily fluid vessel, comprising:

providing a first catheter, and inserting the first catheter into the vessel, stopping fluid flow in the vessel;

after stopping fluid flow, inserting through the first catheter a malleable substance into the vessel at the location of the perforation;

providing a second catheter having a second membrane attached thereto; and opening a path through the malleable substance by inserting the second catheter into the malleable substance and expanding the second membrane to permit fluid flow through the vessel.

2. The method of claim 1, further including providing a guide wire through the vessel, and wherein the insertion of the first catheter is accomplished by moving the first catheter along the guide wire.

3. The method of claim 1, further including providing a first catheter with a first membrane attached thereto, wherein expansion of the first membrane stops fluid flow in the vessel.

4. The method of claim 1, wherein the malleable substance hardens over time, and wherein the path is opened through the malleable substance after the malleable substance has at least partially hardened.

5. The method of claim 1, wherein the positioning of the second catheter is accomplished by moving the second catheter along a guide wire that is placed in the bodily fluid vessel.

6. The method of claim 1, wherein the first catheter is removed from the vessel prior to moving the second catheter into the vessel.

7. A method of repairing a perforation in a wall of a bodily fluid vessel, comprising:

providing a first catheter, the first catheter having a distal end and a first membrane disposed adjacent the distal end, the first catheter further including first and second passages, wherein the first passage communicates with an aperture in the distal end and the second passage communicates with an inner volume defined by the membrane;

positioning the first catheter into the vessel adjacent the perforation;

inflating the first membrane so that fluid flow through the vessel adjacent the perforation is substantially blocked;

releasing a malleable substance through the second passage and the aperture so that the malleable substance substantially fills a region of the vessel at the perforation without passing through the perforation;

deflating the first membrane;

removing the first catheter from the vessel;

providing a second catheter, the second catheter having a distal end and a second membrane adjacent the distal end of the second catheter, the second catheter further including first and second passages;

introducing the second catheter into the vessel;

positioning the catheter so that the distal end of the second catheter passes through the malleable substance;

expanding the second membrane to press the malleable substance against the wall of the vessel;

deflating the second membrane; and removing the second catheter from the vessel.

* * * * *